United States Patent [19]  [11] 4,456,466
Krass et al.  [45] Jun. 26, 1984

[54] HERBICIDALLY ACTIVE BENZOXAZOLYL ACETOPHENONE OXIME DERIVATIVES

[75] Inventors: Dennis K. Krass, Canal Fulton; Sidney B. Richter, Fairlawn, both of Ohio

[73] Assignee: PPG Industries, Inc., Pittsburgh, Pa.

[21] Appl. No.: 440,052

[22] Filed: Nov. 8, 1982

[51] Int. Cl.$^3$ .............. C07D 263/58; E05B 65/46
[52] U.S. Cl. ............................... 71/88; 548/165; 548/221; 548/326; 424/270; 424/272; 424/273 B
[58] Field of Search ............................ 548/221; 71/88

[56] References Cited

U.S. PATENT DOCUMENTS 4,216,006 8/1980 Farge et al. ..................... 71/88

Primary Examiner—Donald G. Daus
Assistant Examiner—S. A. Gibson
Attorney, Agent, or Firm—Edward J. Whitfield

[57] ABSTRACT

Disclosed are certain herbicidally active benzoxazolyl acetophenone oxime derivatives, herbicidal compositions containing these compounds and the use of such compounds to control the growth of noxious plants, i.e., weeds.

6 Claims, No Drawings

HERBICIDALLY ACTIVE BENZOXAZOLYL ACETOPHENONE OXIME DERIVATIVES

DESCRIPTION OF THE INVENTION

This invention relates to certain benzoxazolyl acetophenone oxime derivatives of the Formula I:

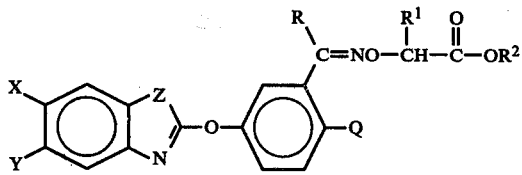

wherein,
R is hydrogen or $C_1$ to $C_3$ alkyl which alkyl may be substituted by halogen, cyano, alkoxy or alkylthio;
$R^1$ is hydrogen or methyl;
$R^2$ is hydrogen, $C_1$ to $C_{10}$ alkyl or an agronomically suitable ionic species (e.g., sodium, potassium or ammonium);
Q is halogen (e.g., chlorine, bromine or fluorine), nitro, or cyano;
X and Y are the same or different and represent hydrogen, halogen (e.g., chlorine, bromine, or fluorine), or $C_1$ to $C_4$ alkoxy; and
Z is oxygen, sulfur, —NH—, or —$NR^3$— where $R^3$ is $C_1$ to $C_3$ alkyl.

Preferred compounds of the Formula I are those wherein at least one of X or Y is halogen, e.g., chlorine, or trifluoromethyl, R is methyl, $R^1$ is hydrogen, $R^2$ is $C^1$ to $C^4$ alkyl, Z is oxygen and Q is nitro.

Compounds of this invention embodied in the Formula I are believed to be herbicidally active and would be effective in regulating growth of a wide variety of undesirable plants, i.e., weeds, when applied, in herbicially effective amount, to the growth medium prior to emergence of the weeds or to the weeds subsequent to emergence from the growth medium. The term "herbicidally effective amount" is that amount of compound or mixture of compounds of this invention required to so injure or damage weeds such that the weeds are incapable of recovering following application. The quantity of compound or mixture of compounds of this invention applied in order to exhibit a satisfactory herbicidal effect may vary over a wide range and depends on a variety of factors, such as, for example, hardiness of a particular weed species, extent of weed infestation, climatic conditions, soil conditions, method of application and the like. Typically, as little as one or less pound per acre of compound or mixture of compounds of this invention would be expected to provide satisfactory weed control, although in some instances application rates in excess of one pound per acre, e.g., up to 5 pounds per acre might be required. Of course, the efficacy of a particular compound against a particular weed species may readily be determined by routine laboratory or field testing in a manner well known to the art.

A compound or compounds of this invention may, of course, be used as such or in formulation with agronomically acceptable adjuvants, inert carriers, other herbicides, or other commonly used agricultural compounds, for example, insecticides, fungicides, stabilizers, safeners, fertilizers or the like. The compounds of this invention alone or in formulation with other agronomically used materials are typically applied in the form of dusts, granules, wettable powders, solutions, suspensions, aerosols, emulsions, dispersions or the like in a manner well known to the art. When formulated with other typically used agronomically acceptable materials, the amount of compound or compounds of this invention may vary over a wide range, for example, from about 0.05 to 95 percent by weight on weight of formulation. Typically, such formulations would contain from about 5 to 75 percent by weight of compound or compounds of this invention.

A compound or compounds of this invention are effective in controlling a variety of common broadleaved and grassy weeds at application rates of only a few grams per acre either pre- or postemergent. Exemplary of weeds that may be effectively controlled by the application of compounds of this invention are barnyard grass (*Echinochloa crusgalli*), crabgrass (*Digitaria sauguinalis*), coffeeweed (*Daubentonia punices*), jimsonweed (*Datura stamonium*), johnsongrass (*Sorghum halepense*), tall morningglory (*Ipomoea purpurea*), wild mustard (*Brassica caber*), teaweed (*Sida Spinosa*), velvetleaf (*Abutilin Theophrasti*), wild oat (*Avena fatua*), yellow foxtail (*Setaria glauca*), yellow nutsedge (*Cyperus esculentus*) and the like.

The Formula I compounds of this invention may be prepared by reacting an appropriately substituted benzoxazolyl of the Formula II:

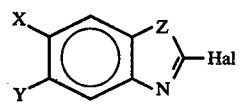

wherein X and Y and Z are as previously defined and Hal is halogen, e.g., chlorine, with an alkali metal, e.g., potassium, salt of an aldehyde or ketone of the Formula III:

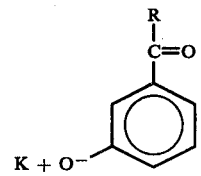

wherein R is as previously defined, to form a compound of the Formula IV:

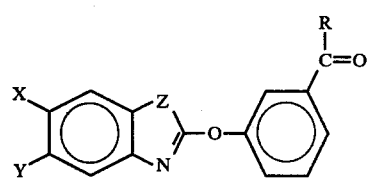

The Formula IV compound is then nitrated, halogenated or cyanated, in known fashion, depending on the desired Q substituent and is then reacted with hydroxylamine or a salt thereof to form the corresponding oxime of the Formula V:

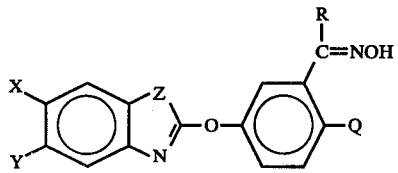

The Formula V compound is then reacted with an -halocarboxylate of the Formula VI:

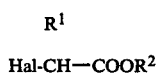

wherein:
Hal is halogen, e.g., bromine or chlorine; and
R¹ and R² are as previously defined, to form an invention compound of the Formula I.

The foregoing mode of synthesis is illustrated more specifically as follows:

(a) A reactor is charged with 5.22 grams (0.03 mole) of the potassium salt of 3-hydroxyacetophenone (Formula III Compound) and 35 milliliters of dimethylsulfoxide. To this mixture is added 5.61 grams (0.03 mole) of 2,5-dichlorobenzoxazole (Formula II Compound) in 15 milliliters of dimethylsulfoxide. After stirring at about 145° C. for about 7 hours, the reaction mixture is stripped of solvent and the residue is dissolved in a mixture of methylene chloride and water. The organic phase is washed with 0.25 normal sodium hydroxide solution and dried over anhydrous magnesium sulfate. Filtration and removal of solvent affords 3-(5-chloro-2-benzoxazolyloxy)acetophenone (Formula IV Compound).

(b) A reactor is charged with 4.0 grams (0.014 mole) of 3-(5-chloro-2-benzoxazolyloxy)acetophenone, prepared as described in part (a), and 10 milliliters of ethylene dichloride. To this solution is added 16 milliliters of concentrated sulfuric acid and the mixture is cooled in an ice bath. To this cold mixture is added incrementally over a 25 minute period, 1.52 grams (0.015) of potassium nitrate, the temperature of the mixture being maintained below 5° C. After stirring for 2 hours at 0° C., the mixture is adjusted to a pH of about 6 with 40 percent aqueous sodium hydroxide solution and phase separated. The aqueous phase is extracted with methylene chloride and the combined organic phases are dried and stripped of solvent. The oily residue is subjected to column chromatography (silica gel) affording 5-(5-chloro-2-benoxazolyloxy)-2-nitroacetophenone.

(c) A reactor, provided with a Dean-Stark trap and condenser, is charged with 3.32 grams (0.01 mole) of 5-(5-chloro-2-benzoxazolyloxy)-2-nitroacetophenone, prepared as described in part (b), and 20 milliliters each of benzene and ethanol. To this solution is added 1.38 grams (0.02 mole) of hydroxylamine hydrochloride and 2.02 grams (0.02 mole) of triethylamine. After 18 hours at reflux, the reaction mixture is stripped of solvent and the residue is dissolved in a mixture of methylene chloride and water. The organic phase is washed with water and dried over anyydrous magnesium sulfate. Filtration and solvent removal affords 5-(5-chloro-2-benzoxazolyloxy)-2-nitroacetophenone oxime (Formula V Compound).

(d) To a reactor containing 20 milliliters of methanol and 0.23 gram (0.01 mole) of metallic sodium is added 3.47 grams (0.01 mole) of 5-(5-chloro-2-benzoxazolyloxy)-2-nitro-acetophenone oxime, prepared as described in part (c). After dissolution, is added, in one portion, 1.67 grams (0.011 mole) of methylbromoacetate (Formula VI Compound). After stirring for 20 hours at ambient temperature, the reaction mixture is stripped of solvent and the residue is dissolved in a mixture of methylene chloride and water. The organic phase is washed with water and saturated aqueous sodium chloride solution and dried over anhydrous magnesium sulfate. The residue is filtered, dried, chromatographed on silica gel and eluted with 95:5 (volume/volume) benzene/ethanol/mixture. Solvent removal affords a mixture of the desired E and Z isomers of 5-(6-chloro-2-benzoxazolyloxy)-2-nitroacetophenone oxime-O-(acetic acid, methyl ester).

The manner of preparing a specific compound within the scope of this invention is described in some detail by the foregoing, and it is to be understood that other Formula I compounds can be prepared in like manner by simply varying the choice of starting materials. The compounds of this invention may also be prepared by alternative methods. For example, the compound 5-(5-chloro-2-benzoxazolyloxy)-2-nitroacetophenone oxime-O-(acetic acid, methyl ester), prepared as described hereinabove, may also be prepared as follows:

Substantially equimolar amounts of 5-chloro-2-hydroxy benzoxazole and 5-fluoro-2-nitroacetophenone are reacted, in an inert organic solvent, e.g., dimethylsulfoxide, in the presence of potassium carbonate giving 5-(5-chloro-2-benzoxazolyloxy)-2-nitro acetophenone. The 2-nitroacetophenone is then reacted with a suitably substituted aldoxime or ketoxime-O-alkanoic acid, e.g., isopropylidene aminooxyacetic acid in an organic liquid, e.g., acetic acid, reaction medium, and in the presence of a strong organic or mineral acid, e.g., p-toluene sulfonic acid, sulfuric acid or hydrochloric acid, to give 5-(5-chloro-2-benzoxazolyoxy)-2-nitroacetophenone oxime-O-acetic acid. Esterification with an aliphatic alcohol, e.g., methanol, in the presence of a strong organic or mineral acid affords the corresponding 5-(5-chloro-2-benzoxazolyloxy)-2-nitroacetophenone oxime-O-(acetic acid, methyl ester).

Although the invention has been described in some detail with reference to certain embodiments thereof, it is to be understood that it is not intended to be so limited, since many variations may be made therein by those skilled in the art without departing from the spirit and scope thereof as defined in the appended claims.

We claim:

1. A compound of the formula:

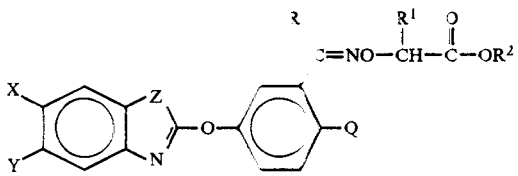

wherein:
R is hydrogen or C₁ to C₃ alkyl which alkyl may be substituted by halogen, cyano, alkoxy or alkylthio;
R¹ is hydrogen or methyl;
R² is hydrogen, C₁ to C₁₀ alkyl or an agronomically suitable ionic species;
Q is halogen, nitro, or cyano;

X and Y are the same or different and represent hydrogen, halogen, $C_1$ to $C_4$ alkyl, $C_1$ to $C_4$ haloalkyl or $C_1$ to $C_4$ alkoxy; and Z is oxygen.

2. A compound of claim 1 wherein at least one of X or Y is halogen or trifluoromethyl.

3. A compound of claim 1 wherein Z is oxygen.

4. A compound of claim 1 wherein Q is nitro.

5. In a method of controlling weed growth wherein a herbicidally effective amount of a herbicide is applied either to the growth medium prior to emergence of the weeds therefrom or to the weeds subsequent to their emergence from the growth medium wherein the improvement resides in using as the the herbicide compound or mixture of compounds defined in claim 1.

6. A herbicidal composition containing an inert carrier and a herbicidally effective amount of a compound or mixture of compounds defined in claim 1.

* * * * *